US012721802B2

(12) United States Patent
Costo Lucco et al.

(10) Patent No.: US 12,721,802 B2
(45) Date of Patent: Sep. 1, 2026

(54) FLEXIBLE AND SOLID MAKE-UP PRODUCT, AND A SWATCH OF MAKE-UP PRODUCTS

(71) Applicant: CHROMAVIS S.p.A., Offanengo (CR) (IT)

(72) Inventors: Davide Costo Lucco, Castelleone (CR) (IT); Giordano Valsecchi, Trescore Cremasco (CR) (IT)

(73) Assignee: CHROMAVIS S.p.A., Offanengo (IT)

( * ) Notice: Subject to any disclaimer, the term of this patent is extended or adjusted under 35 U.S.C. 154(b) by 611 days.

(21) Appl. No.: 18/118,854

(22) Filed: Mar. 8, 2023

(65) Prior Publication Data

US 2023/0285266 A1 Sep. 14, 2023

(30) Foreign Application Priority Data

Mar. 9, 2022 (IT) ........................ 102022000004508

(51) Int. Cl.

| | |
|---|---|
| ***A61K 8/73*** | (2006.01) |
| ***A61K 8/02*** | (2006.01) |
| ***A61K 8/25*** | (2006.01) |
| ***A61K 8/34*** | (2006.01) |
| ***A61K 8/37*** | (2006.01) |
| ***A61K 8/86*** | (2006.01) |
| ***A61Q 1/10*** | (2006.01) |

(52) U.S. Cl.

CPC .............. *A61K 8/73* (2013.01); *A61K 8/0245* (2013.01); *A61K 8/25* (2013.01); *A61K 8/342* (2013.01); *A61K 8/37* (2013.01); *A61K 8/375* (2013.01); *A61K 8/86* (2013.01); *A61Q 1/10* (2013.01); *A61K 2800/43* (2013.01); *A61K 2800/87* (2013.01)

(58) Field of Classification Search

CPC .......... A61K 8/73; A61K 8/0245; A61K 8/25; A61K 8/342; A61K 8/37; A61K 8/375; A61K 8/86; A61K 2800/43; A61K 2800/87; A61K 2800/882; A61K 8/022; A61K 8/345; A61Q 1/10; A61Q 1/12

See application file for complete search history.

(56) References Cited

U.S. PATENT DOCUMENTS

| | | | |
|---|---|---|---|
| 9,357,826 | B2 * | 6/2016 | Caprarotta et al. |
| 9,713,580 | B2 * | 7/2017 | Sunkel et al. |

FOREIGN PATENT DOCUMENTS

| | | | |
|---|---|---|---|
| EP | 2189150 | * | 5/2010 |
| JP | 2002265314 | * | 9/2002 |
| JP | 2002265314 | A | 9/2002 |

OTHER PUBLICATIONS

6 Makeup tips that will seriously improve your shopping experience: Refinery29.com/en-us/makeup-swatches-guide#slide-1, 2021 (Year: 2021).*

Create Swatches on the Arms for Beauty Products (Isa-Aydin), (Year: 2016).*

English Translation of JP2002265314A, Sep. 18, 2002, Someta et al.*

MINTEL; Jan. 3, 2008 (Jan. 3, 2008), anonymous: "Impression Eyes (52 Green)", XP055975246, Database accession No. 836819 * abstract *.

MINTEL; Dec. 10, 2019 (Dec. 10, 2019), anonymous: "Mothership: Divine Rose 10 Eye Shadows", XP055975247, Database accession No. 7112049 * abstract *.

* cited by examiner

*Primary Examiner* — Robert A Wax
*Assistant Examiner* — Kimberly Barber
(74) *Attorney, Agent, or Firm* — Dickinson Wright PLLC; Andrew D. Dorisio; Nicholas P. Coleman

(57) ABSTRACT

The present invention relates to a make-up product in a powdered solid form, such as an eyeshadow, blush, foundation, concealer, highlighter, for the face or body, blush, lipstick in a powdered form, or a primer, characterized by a high degree of flexibility and resistance to deformation and impact.

19 Claims, 2 Drawing Sheets

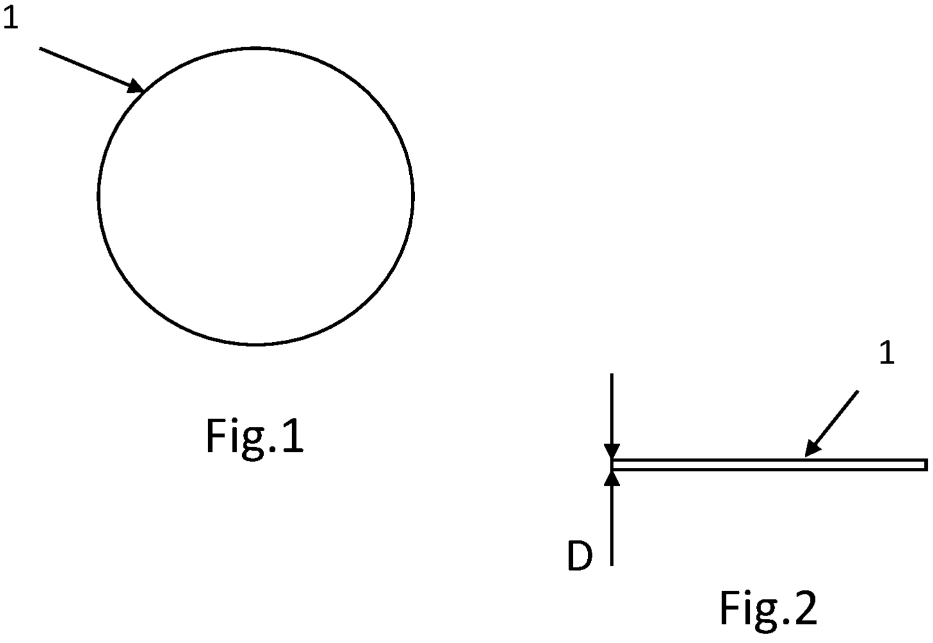
Fig.1
Fig.2
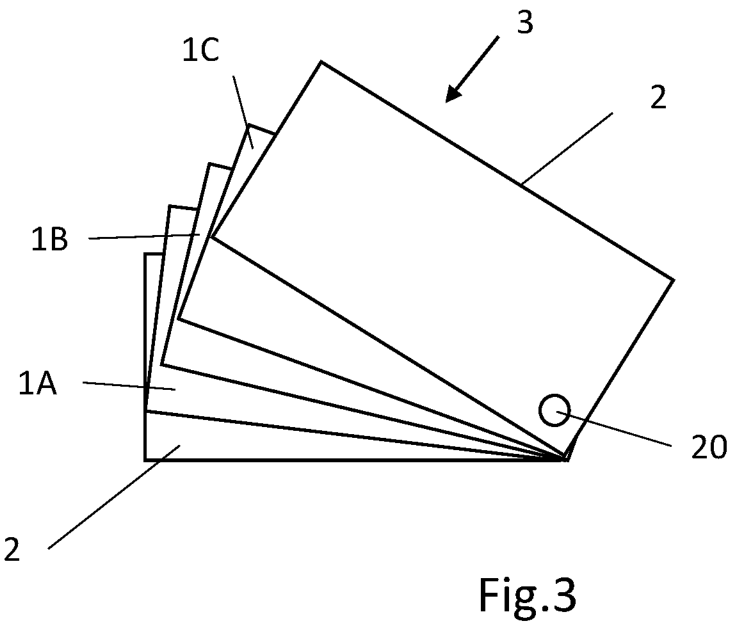
Fig.3

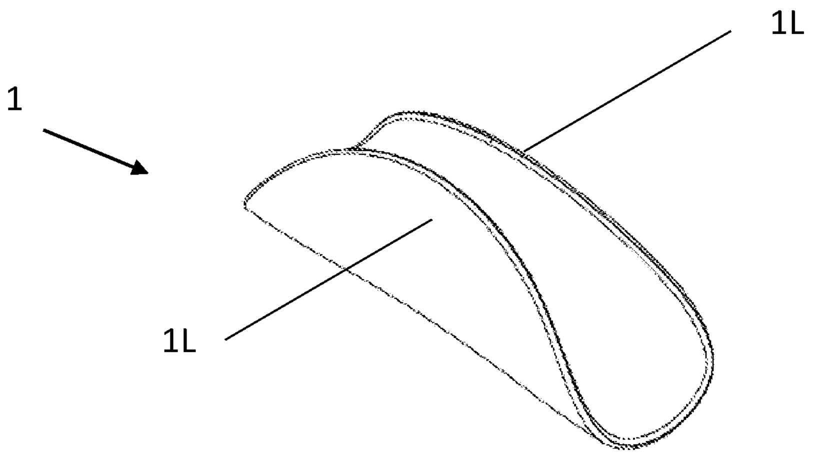
Fig.4
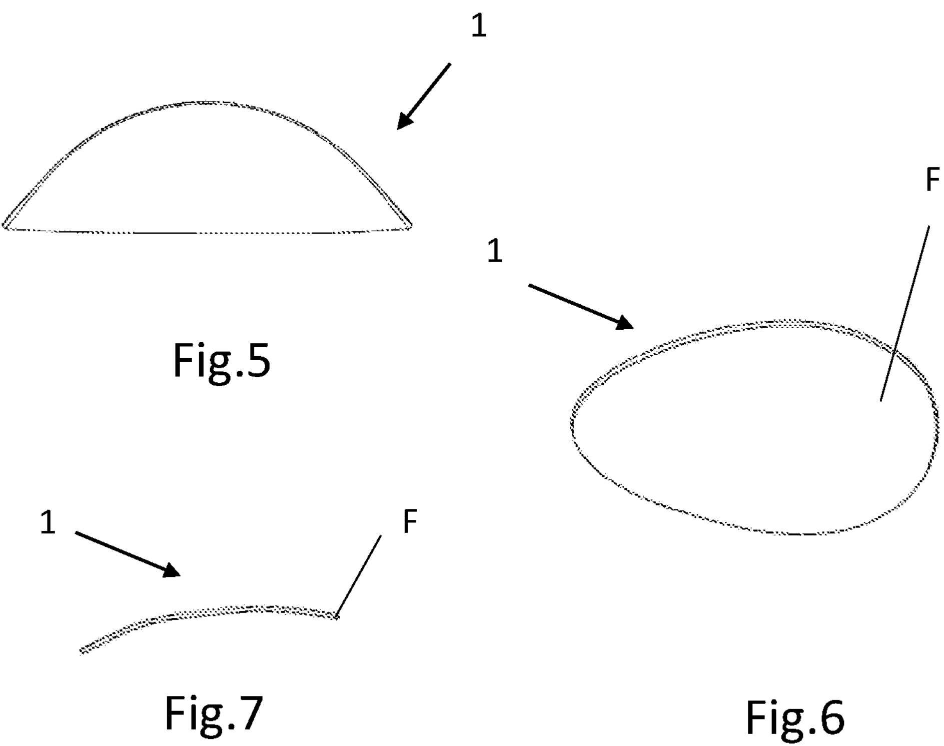
Fig.5
Fig.7
Fig.6

FLEXIBLE AND SOLID MAKE-UP PRODUCT, AND A SWATCH OF MAKE-UP PRODUCTS

This application claims the benefit of Italian Patent Application No. 102022000004508 filed on Mar. 9, 2022, the disclosure of which is incorporated herein by reference.

FIELD OF THE INVENTION

The present invention relates to a cosmetic product, in particular for make-up, and to a method for making it.

The invention also relates to a swatch of makeup products, comprising a plurality of said products having different colors and, optionally, different makeup effects.

Specifically, the present invention relates to a makeup product in a solid form based on a makeup powder, such as a eyeshadow, blush, foundation, concealer, highlighter, for the face or for the body, a blush, a lipstick in a powder form, or a primer, characterized by a high degree of flexibility and resistance to deformation and impact, which makes it practically inert to the drops and external stresses during use.

BACKGROUND ART

Among cosmetic products, eye-making products, such as for example eyeshadows, generate a large part of the overall turnover of the cosmetic market. There are different types of eyeshadow, which can be produced according to different technologies:

1. compact eyeshadows, prepared by a process comprising grinding powders (fillers and pigments) together with suitable binding compounds, sieving powders to obtain a uniform particle size, and subsequent compacting under pressure in a metal container (generally aluminum) to form a “compact” cake;
2. cast eyeshadows, obtained by a process which comprises melting waxes and oils in melting pans, followed by the addition of a dispersion of suitably calendered pigments inside the bulk; the bulk is then allowed to solidify into cakes which are melted and dosed in the metal base (in a pot or other suitable container), where they are allowed to solidify again, to obtain the finished product;
3. “mousse” or cream, prepared by mixing in melting/turboemulsifiers oils of different kinds, gelling agents and elastomers, with pigments and viscosity control agents, to obtain a product of soft, aerated and semi-solid consistency which is typically dosed in a jar or in a tube;
4. cooked eyeshadows prepared by a process which comprises grinding powders (fillers and pigments) together with suitable binding compounds (containing water and other volatile substances), the subsequent compacting on a terracotta base, which is put in the oven to dry;
5. extruded eyeshadows prepared by a process comprising mixing powders (fillers and pigments) together with suitable binding compounds (containing water and other volatile substances), the subsequent extrusion in the form of a plate which is suitably shaped. The shaped part is placed in an aluminum bottom or other material, compacted and put to dry in an oven. These different preparation methods are generally applicable to solid cosmetic products based on dust. The above examples, referred to the sole category of eyeshadow, can also be extended to other types of products, such as fard, primer, bronzer, face/body lighting, foundation, and the like.

The substantial difference between the various products obtainable by the above described processes lies in their organoleptic and applicative characteristics, i.e. the overall sensory characteristics perceived by the user during use, normally referred to as “textures”.

The texture mainly concerns:

- the appearance of the product, which has for example a dusty consistency, compacted, shiny and smooth products in the case of hot-rolled or cream-filled, soft and aerated products (because the product assumes a spongy consistency by evaporation of the solvents in the drying process) in the case of cooked or extruded products;
- the tactile sensation, when the product is taken for use, is for example dry and dusty in the case of compact, creamy and oily products in the case of cast or cream products, and creamy in the case of cooked and extruded products;
- the tactile sensation during the spreading is typically dusty and dry in the case of compacted products, smooth and adherent in the case of hot-cast products, and soft and rubbery in the case of mousse products;
- the aesthetic result of the product, which can vary from dusty and matt to be pearled and metallic;
- the duration, since the various textures have different degrees of “persistence” on the skin over time; long-lasting products have, for example, a longer residence time than the average of analogous products.

Compact products are very advantageous in that they occupy little space, they are easier to pack and transport, both at industrial level and for the end user (for example in journeys). Furthermore, the compact products are easier to apply without touching the cosmetic product with the hands and, being solid, the risk of unwanted stains on the user’s skin or clothing is reduced.

However, the texture of the compact products is not comfortable for subjects with dry skin and poor duration. Moreover, they are not very elastic and ductile from the production point of view, if for example it is desired to form ridges on the surface of the product outside the bottom. Moreover, such products tend to break easily when they are subjected to impacts, compromising their use: in fact, it is impossible to obtain a homogeneous pick up, precisely because of the breaking of the wafer that produces dust and fragments.

SUMMARY OF THE INVENTION

The object of the present invention is to provide a cosmetic product, in particular for make-up, in a solid form based on makeup powders, which maintains the above mentioned advantages for the compact products, but at the same time having a high degree of flexibility and resistance to deformation and impact.

This and other objects are achieved by a cosmetic product, in particular for make-up, according to the technical teachings of the appended claims.

The present invention is therefore directed to a cosmetic product, in particular for make-up, in a solid form based on makeup powders, flexible and resistant to deformation and impact. Preferably said article is a eyeshadow, blush, foundation, concealer, highlighter, for the face or body, a blush, a lipstick in powder form, or a primer; more preferably said product is a eyeshadow. The present invention is also directed to a process for the preparation of said makeup product, to a method of applying said cosmetic product to the skin and to a swatch of makeup products according to the invention. The invention also relates to a swatch of makeup products.

BRIEF DESCRIPTION OF THE FIGURES

Further characteristics and advantages of the invention will become apparent from the description of preferred but not exclusive embodiments of the invention, illustrated by way of non-limiting examples in the accompanying drawings, wherein:

FIG. 1 shows, from above, a punched make-up product in the form of a disc, according to a preferred embodiment of the present invention;

FIG. 2 shows a side view of the make-up product of FIG. 1;

FIG. 3 shows a swatch which can comprise a plurality of cosmetic products with different colors or effects;

FIG. 4 shows a perspective view of the product of FIG. 1, which is deformed substantially in an elastic manner until it has a U-shape;

FIG. 5 is a side view of the product in the shape of FIG. 4;

FIG. 6 is a perspective view of the product of FIG. 1 slightly deformed under its own weight; and FIG. 7 is a side view of the product of FIG. 6.

DETAILED DESCRIPTION OF THE INVENTION

The cosmetic product 1 (or make-up product) of the present invention in a flexible solid form, comprises a mixture of cosmetic powders and:

a) 0.1-15% by weight of at least one carrageenin, based on the weight of the cosmetic product.

Carrageenins are a family of compounds of a polysaccharide nature (CAS Number: 9000-07-1), obtained by boiling red algae of the rocky coast of the North Atlantic (Chondrus criSp11S and Gigartina mamitiosa, also known by the names of musk of Ireland, marine lichene or carrageen).

Three types of carrageenins are mainly identified: kappa (k-), iota (i-) and lambda (l-), which differ from one another in the number and position of the sulfate groups and in the bond that joins the individual monomers. In principle, the greater the number of sulfates, the lower the viscosity-increasing capacity.

For the purposes of the present invention, carrageenins of the iota (i-) type are preferred, due to their ability to generate soft and extremely elastic gels. The addition of glucose and potassium chloride increases this characteristic.

Also, carrageenins of the kappa type (k-) can be used, the peculiarity of which is to stabilize the formulation and improve the texture of the product.

Preferably, at least two different carrageenins are present, having different viscosifying capacity.

There are several commercial carrageenins, having specific viscosity and properties, which can be used together in the composition of the product of the invention. Particularly preferred are the carrageenins marketed as Safic care t ck-1 by Safic-alcan, Flower Tales Cosmetics carrageenan iota, and GENUVISCO@ CG-131, CP Kelco carrageenin iota.

By the term "mixture of cosmetic powders", it is meant, depending on the makeup product considered, a mixture of ingredients in a powdery solid form which typically constitutes such makeup products.

For example, the cosmetic powders may comprise ingredients such as talc, Mica, bismuth chloride oxide (CI77163), iron oxides (CI77491-2-9), Ultramarine Blue (CI77007), Manganese Violet (CI77742), Chromium hydroxide (CI77289), Chromium oxide (CI77288), Ferric ammonium ferrocyanide (CI77510), Titanium dioxide (CI77891), D&C Red7 CA Lake, D&C Red 1 9 A1 Lake, D&C Red6 Ba Lake, D&C Red3 A1 Lake, D&C Red9 BA Lake, D&C Red21 A1 Lake, D&C Yellow5 A1 Lake, D&C Red30 A1 Lake, D&C Yellow 10 A1 Lake, D&C Red27 A1 Lake, D&C Yellow5 A1 Lake, D&C Orange5, FD&C Yellow6 A1 Lake, FD&C Blue1 A1 Lake, D&C red36 A1 Lake, Carmine (CI75470), Fluorflogopite (synthetic Mica), Boron nitride, Borosilicate Aluminum calcium, Magnesium aluminum borosilicate.

(In the above list the term "CI" in brackets represents the reference Color Index; CTFA NAME for organic lacquers are also present.)

Preferably, the cosmetic product in a flexible solid form of the invention comprises a mixture of cosmetic powders and:

a) 0.1-15% by weight of at least one carrageenin, on the weight of the cosmetic product, said cosmetic product further having at least one of the following technical features:

hardness [shore A]: 20-60 (ASTM D2240)

tensile strength [N/mm2]: 2-10 (ASTM D412)

elongation [%]: 5-15 (ASTM D412)

tear strength [N/mm]: 10-40 (ASTM D624).

In fact, these technical features (preferably all) allow the product to remain suitably flexible, therefore resistant to impact and pleasant at touch, while remaining solid and therefore easy to handle.

More preferably, the product of the invention comprises 40-60% by weight of a mixture of cosmetic powders and:

a) 0.5-10% by weight of at least one carrageenin;

b) 0.05-5% by weight of a non-emulsifying ester selected from isonononyl isonononanoate, isodecyl neopentanoate, octyldodecyl neopentanoate, isostearyl isostearate, isopropyl, myristeristearate, myristate, myristate, myristeristearate, myri Isocethyl stearate, and mixtures thereof;

c) 0.1-5% by weight of ether methyl glucose dioleate;

d) 0.1-5% by weight of two or more of glyceryl stearate, Behenyl alcohol, palmitic acid, stearic acid, lecithin, Lauryl alcohol, myristyl alcohol, and cetyl alcohol;

e) 5-10% by weight of glycerin;

based on the weight of the product.

In preferred embodiments, said non-emulsifying ester b) is isonononyl isononanoate.

In preferred embodiments, ingredient d) is a mixture of glyceryl stearate, Behenyl alcohol, palmitic acid, stearic acid, lecithin, Lauryl alcohol, myristyl alcohol, and cetyl alcohol.

The make-up product 1 of the present invention is characterized by a unique texture, which includes various features usually associated with different types of products, which have never existed before in a single formula. For example, said product has a compact appearance, but has a consistency similar to that of an extruded product when it is taken, comparable to that of a cast product when it is laid on the skin.

Advantageously, the makeup product 1 of the invention is inert when dried (i.e., it is not staining, nor releases components if placed in contact with a dry surface, including the skin). When instead it is wetted, i.e. placed in contact with polar substances, such as water, glycols, or alcohols, it immediately turns to be writing (i.e. it releases part of the product, for example it releases color on the skin when applied).

Owing to these peculiar characteristics, the makeup product can be transported and touched without undesirably releasing color, while it is sufficient to moisten it to make it usable for makeup or make-up operations.

The present invention is therefore also directed to the use of said make-up product 1 for making-up the skin by a method comprising the following steps in series:

moistening the makeup product 1 described above with a polar substance, preferably water, and applying the makeup product released from the makeup product, thus wetted, onto the skin.

When used to makeup the skin, the makeup product 1 of the invention forms a perfectly adherent but imperceptible making-up film on the skin, which also has a long lasting. The cosmetic product 1 (or for the make-up) of the invention, being inert when dried and being deformable (in a substantially elastic manner), resistant to impact and obtainable in a very thin sheet, can also be advantageously marketed in a multi-color packaging (FIG. 3), similar to a RAL sample book or a swatch, easily transportable and easily usable to make available immediately the desired makeup effect (or color of the make-up).

For example, it is possible to provide a swatch of different colors or makeups, as exemplified in FIG. 3, in which each of the cards (each formed by a make-up product 1) that make up the swatch comprises makeup products having different color and/or makeup effect.

Therefore, the present invention is also directed to a swatch of makeup products 1 comprising a plurality of makeup products (La, 1B, 1C, . . . ) according to the invention, wherein each card is of a different color or provides a different makeup effect when applied to the skin according to the method described above, wherein said cards are sheets of a thickness D of 0.5-1.5 mm, optionally shaped.

In the example shown in FIG. 3, the shape of the cards is rectangular, and the card swatch is held together by a hinge 20.

Clearly, however, the swatch 3 can comprise a plurality of makeup products (1A, 1B, 1C, . . . ) even with different shapes and fixed to one another in a different way by a hinge. For example, the various makeup products can be bound together and folded like bellows, fan, etc.

Advantageously, the end elements 2 of the swatch 3 can be sheets of cardboard, cardboard, plastic, etc., possibly decorated or bearing a logo, lettering, etc.

In this case, each makeup product 1 can provide a hole inside which a hinge pin 20 passes, in common to the plurality of makeup products 1*a*, 1B, 1C, . . . of the swatch 3 (and also in common to the end elements 2).

In the example of FIG. 3, three makeup products are shown, but clearly the number of those that compose the swatch 3 can be any.

The present invention also relates to a process for preparing said cosmetic product 1 (or make-up product), in which the conventional step of providing the mixture of cosmetic powders, which can be prepared for example according to what is described in the patent EP2189150B1, it is followed by further specific steps for the present process which contribute to the formation of the desired product.

In particular, the process for preparing the product of the present invention comprises the following steps:

i. providing a mixture of cosmetic powders;

ii. mixing said cosmetic powders with an emulsion comprising water and at least one carrageenan, preferably in a kneading machine at a speed of 5-500 rpm, thus obtaining a paste;

iii. spreading a layer of said paste on a solid flat support;

iv. letting the paste dry by placing said support in an oven;

v. removing the layer of thus dried paste from the support, thus obtaining the cosmetic product in a solid form;

vi. optionally, die-cutting the cosmetic product in a solid form, thus obtaining the cosmetic product of the desired shape.

In step i., the cosmetic powders are preferably provided in the form of a homogeneous mix by using a high-speed mixer.

Preferably, step ii. of the process is carried out in a suitable turboemulsifier. Preferably, in step ii., the cosmetic powders and the emulsion are mixed in a weight ratio of 10:90 to 50:50, more preferably 10:90 to 40:60. In preferred embodiments, the cosmetic powders and the emulsion are mixed in a weight ratio of about 30:70.

More preferably, in step ii., said emulsion comprises water and:

a) 0.5-10% by weight of at least one carrageenan;

b) 0.05-5% by weight of a non-emulsifying ester selected from isononyl isonononononanoate, isodecyl neopentanoate, octyldodecyl neopentanoate, isostearyl isostearate, isopropyl myristate, Isocethyl stearate, and mixtures thereof;

c) 0.1-5% by weight of ether methyl glucose dioleate;

d) 0.1-5% by weight of two or more of glyceryl stearate, Behenyl alcohol, palmitic acid, stearic acid, lecithin, Lauryl alcohol, myristyl alcohol, and cetyl alcohol;

e) 1-10% by weight of glycerin;

based on the weight of the emulsion.

In preferred embodiments, in step ii., said emulsion comprises water and:

a) 0.5-5% by weight of at least one carrageenin;

b) 0.05-5% by weight of a non-emulsifying ester selected from isonononyl isonononononanoate, isodecyl neopentanoate, octyldodecyl neopentanoate, isostearate, isopropyl myristate, Isocethyl stearate, and mixtures thereof;

c) 0.5-3% by weight, preferably about 2% by weight, of a dioleate methyl glucose ether, preferably PEG-120 methyl glucose dioleate, such as Glucamate™ DOE-120 obtainable from Lubrizol;

d) 0.5-3% by weight, preferably about 2% by weight, of glyceryl stearate, Behenyl alcohol, palmitic acid, stearic acid, Lecithin, lauryl alcohol, myristyl alcohol, and cetyl alcohol, such as for example the mixture known by the trade name of Sepid™ 141 and produced by Ashland, e) 1-10% by weight of glycerin, based on the weight of the emulsion.

Preferably, in step iv., the mixture is dried in an oven at a temperature of 25-70° C., more preferably 30-50° C., even more preferably at about 40° C. for a few hours, preferably for 5-10 hours, even more preferably for about 7 hours.

When drying is finished, the cosmetic product 1 is obtained in a solid form, which can be further shaped/punched in the desired form, for example circles, rhombuses, stars, etc.

The process for preparing the flexible solid cosmetic product is preferably a process for preparing a flexible solid eyeshadow, wherein the cosmetic powders provided in step i. are obtained by mixing the constituents of the eyeshadow (such as: dyes, talc, mica, silica, beads) and sieving the resulting mix, to make the particle size homogeneous. Preferably, the mixture of cosmetic powders comprises pearlescent pigments, typically formed by mica coated with titanium oxide, in a concentration of 20 to 70% by weight, based on the total weight of the powder mixture.

In another aspect, the present invention relates to a flexible solid cosmetic product, obtainable by the preparation process described above, said cosmetic product being in the form of a sheet of thickness D of 0.5 to 1.5 mm.

Preferably, said thickness D is 0.5 to 1 mm, more preferably greater than or equal to 0.5 mm and less than or equal to 1 mm. In preferred embodiments, said product may be a disc of the thickness indicated above, as exemplified in FIGS. 1 and 2.

The diameter of the disc may be of 5 mm to 60 mm, preferably of about 36 mm. Preferably, the flexible solid cosmetic product, obtainable by the preparation process described above, further has at least one of the following technical features:

hardness [Shore A]: 20-60 (ASTM D2240)
tensile strength [N/mm2]: 2-10 (ASTM D412)
elongation [%]: 5-15 (ASTM D412)
tear strength [N/mm]: 10-40 (ASTM D624).

The set of all these features is particularly advantageous. Differently from the compact products known in the art, the product of the present invention, thus obtained, can be directly placed in an envelope of flexible material, such as paper or silicone, without requiring a rigid bottom to prevent its breakage, because advantageously such a product is flexible and impact resistant. It can then be handled directly, without the need for protective casings or containers.

In fact, as already discussed, the composition of the product and the preparation process allow to obtain a product, also having a very reduced thickness D, even less than or equal to 1 mm, advantageously without the need to compact the final product.

At the touch, the product 1 has a solid, almost rubbery, dry, but extremely flexible and resistant form, at the same time.

As said, since it is flexible, it is not necessary to dose the product in a rigid primary package, such as a bottom, a can, a flaconette or a tube, since it maintains a high resistance to impact, deformation and traction (contrary to the compact, cooked or extruded products). This is for the benefit of the environment.

The extraordinary flexibility of the product can be clearly seen from the analysis of FIGS. 4 to 7.

In FIG. 4, it can be seen that the product can be bent substantially in a U-shape without breaking or creating cracks on its surface. The bending can be obtained for example by applying a slight force (for example with the fingers) at the edges 11. Once the force on the flaps has ceased, the product returns, substantially in an elastic manner, in its original configuration, and therefore substantially flat, as in FIG. 6.

After bending, only slight or no deformations remain to the product, which can be however flattened with a very slight pressure exerted with the fingers.

For example, in FIG. 6, such slight deformations of a product substantially gripped in the area indicated as F.

As shown in FIG. 7, by virtue of its own weight, can be seen when it is gripped in a cantilevered manner at, for example, the region F, the product bends slightly until it is slightly concave downwards.

All this without breaking, without cracking or releasing dust or traces of product (unless moistened).

Moreover, the product has a high resistance to thermal changes and above all to heat, unlike cast or cream products.

A further advantage is given by the fact that the product 1 does not release color unless it has been wetted with a polar solvent, for example with water, or glycols, preferably at least of the pentylene type.

Using water, the product on the skin dries even in a very short time (from 1 to 3 minutes).

It is to be understood that all the aspects identified as preferred and advantageous for the cosmetic product are to be considered likewise preferred and advantageous also for the uses and the process of preparation thereof, as well as for the product obtainable from this process.

It is also to be understood that all combinations of the preferred aspects of the cosmetic product of the invention, as well as of the uses and the preparation process, as reported above, are to be considered as described herein.

Various embodiments of the invention have been described, but others can be conceived using the same innovative concept.

Examples of embodiments of the present invention are given below by way of illustration.

EXAMPLES

Example 1

An eyeshadow according to the present invention is prepared.

The following is the composition of the starting ingredients:

| | Ingredients | % by weight (based on the total ingredients' weight) | Commercial product |
|---|---|---|---|
| 1 | CI 77891 (titanium dioxide)<br>Tin oxide<br>mica | 30.000 | |
| 2 | potassium sorbate | 0.275 | |
| 3 | dehydroacetic acid | 0.275 | |
| 4 | isononyl isononanoate | 20.000 | DUB ININ 14031 |
| 5 | glycerine | 4.000 | |
| 6 | tocopherol<br>PEG-120 methyl glucose dioleate | 2.000 | GLUCAMATE ™ DOE-120 |
| 7 | lauryl alcohol<br>glyceryl stearate<br>cetyl alcohol<br>lecithin | 2.000 | PROLIPID ™ 141 |

-continued

| | Ingredients | % by weight (based on the total ingredients' weight) | Commercial product |
|---|---|---|---|
| | palmitic acid<br>myristyl alcohol<br>behenyl alcohol<br>stearic acid | | |
| 8 | Chondrus Crispus<br>glucose<br>potassium chloride | 1.500 | SAFIC' CARE T CK1 |
| 9 | Chondrus Crispus powder | 1.000 | GENUVISCO ® CARRAGEENAN CG-131 |
| 10 | water | 38.950 | |

wherein:

Safic care T CK-1, obtained from Safic-alcan, comprising carrageenin-iota, glucose and potassium chloride;

GENUVISCO@ CG-131, obtained from CP Kelco, carrageenin-iota;

Glucamate™ DOE-120, obtained from Lubrizol, as methyl glucose dioleate ether;

ProLipid™ 141, obtained from Ashland, as a mixture of glyceryl stearate, Behenyl alcohol, palmitic acid, stearic acid, lecithin, lauryl alcohol, myristyl alcohol cetyl alcohol. ProLipid™ 141 is used as a moisturizing agent and to improve the flowability under application.

First, a powder mixture comprising the ingredients 1 to 3 is provided.

This mixture is made in a standard mill. The pearlescent elements are added at the end of the process to maintain their properties unchanged.

An emulsion is separately produced by means of a turboemulsifier comprising the ingredients 4 to 10.

Subsequently, the mixture of powders and the emulsion are mixed by means of a kneading machine of the count type PL760EV 300 at 300 revolutions for a time which can vary indicatively from 5 to 10 minutes.

The obtained mixture (bulk) is spread evenly on a steel tray with a height of about 1 mm.

The tray is placed in an oven to promote the evaporation of the volatile part present in the emulsion at about 40° C. for about 7 h.

When the dry bulk is cooked, it is removed from the tray as a flexible sheet having a thickness of about 1 mm, which is shaped/punched in circles and placed in a flexible silicone bag.

The final composition of the "eyeshadow" product is as follows:

| | Ingredients | % by weight (based on the total ingredients' weight) |
|---|---|---|
| 1 | CI 77891 (titanium dioxide)<br>Tin oxide<br>mica | 49.898 |
| 2 | potassium sorbate | 0.446 |
| 3 | dehydroacetic acid | 0.446 |
| 4 | isononyl isononanoate | 33.200 |
| 5 | glycerine | 6.480 |
| 6 | tocopherol | 3.240 |
| | PEG-120 methyl glucose dioleate | |
| 7 | lauryl alcohol<br>glyceryl stearate<br>cetyl alcohol<br>lecithin | 3.240 |

-continued

| | Ingredients | % by weight (based on the total ingredients' weight) |
|---|---|---|
| | palmitic acid<br>myristyl alcohol<br>behenyl alcohol<br>stearic acid | |
| 8 | Chondrus Crispus<br>glucose<br>potassium chloride | 2.430 |
| 9 | Chondrus Crispus powder | 1.620 |

Example 2

An eyeshadow according to the present invention is prepared.

First, a powder mixture is provided comprising:

| Ingredients | % by weight (based on the total mixture weight) |
|---|---|
| Sodium Dehydroacetate | 0.3 |
| Sorbic acid | 0.4 |
| Magnesium myristate | 3 |
| Zinc Laurate | 3 |
| Zinc Stearate | 0.9 |
| Talc | 30.4 |
| Silica | 2 |
| Mica/pearls | 40 |
| Pigments | 20 |

This mixture is formed in a standard mill. The pearlescent elements are added at the end of the process to maintain their properties unchanged.

An emulsion is separately produced by means of a turboemulsifier comprising the ingredients 4 to 10 indicated in the table of example 1.

Subsequently, the mixture of powders and the emulsion are mixed by means of a kneading machine of the count type PL760EV 300 at 300 revolutions for a time which can vary indicatively from 5 to 10 minutes.

The obtained mixture (bulk) is spread evenly on a steel tray with a height of about 1 mm.

The tray is placed in an oven to favor the evaporation of the volatile part present in the emulsion at about 40° C. for about 7 h.

When the dry bulk is cooked, it is removed from the tray as a flexible sheet having a thickness of about 1 mm, which is shaped/punched in circles and placed in a flexible silicone bag. Example 3.

The process of example 1 is repeated to prepare eyeshadows of different colors using different pigments.

The products thus obtained, shaped in discs of a thickness of about 1 mm, are perforated and aggregated in a swatch via hinging 20.

Example 4

The product obtained in example 1 is placed in contact with water and used to makeup the eyelids of a subject.

The invention claimed is:

1. A process for preparing a cosmetic product for make-up, comprising the steps of:

i. providing a mixture of cosmetic powders;

ii. mixing said cosmetic powders with an emulsion comprising water and at least one carrageenan in a kneading machine at a speed of 5-500 rpm, thus obtaining a paste;

iii. spreading a layer of said paste on a solid flat support;

iv. letting the paste dry by placing said support in an oven;

v. removing the layer of thus dried paste from the support, thus obtaining the cosmetic product in a solid form; and vi. die-cutting the cosmetic product in a solid form, thus obtaining the cosmetic product of a desired shape;

wherein the cosmetic product is in a flexible solid form and comprises the mixture of cosmetic powders and 0.1-15 wt % of the at least one carrageenan, based on a weight of the cosmetic product.

2. The process of claim 1, wherein, in step iii., the paste is spread on the support at a thickness (D) of 0.5-1.5 mm.

3. The process of claim 1, wherein, in step iii., the paste is spread on the support at a thickness (D) of less than or equal to 1 mm.

4. The process of claim 1, wherein, in step iv., the paste is dried in an oven at a temperature of 25-70° C.

5. The process of claim 1, wherein, in step iv., the paste is dried in an oven at a temperature of 30-50° C.

6. The process of claim 1, wherein, in step iv., the paste is dried in an oven at a temperature of about 40° C. for 5-10 hours.

7. A swatch comprising a plurality of cosmetic products (1A, 1B, 1C, . . . ) for make-up, obtained by the process of claim 1, wherein at least one cosmetic product for make-up is of a different color or provides a different make-up effect than the others, when applied to the skin, wherein said cosmetic products for make-up have a thickness of 0.5-1.5 mm.

8. The swatch of claim 7, wherein the plurality of products (1A, 1B, 1C, . . . ) are mutually hinged by a common hinge.

9. The swatch of claim 8, wherein the extremal elements of the swatch are plastic, cardboard or cardboard cards of a shape corresponding to the plurality of cosmetic products (1A, 1B, 1C, . . . ) for make-up.

10. The swatch of claim 8, wherein the plurality of cosmetic products (1A, 1B, 1C, . . . ) for make-up are made up of identical-shaped cosmetic products for make-up.

11. The process of claim 1, wherein said at least one carrageenan is carrageenan-iota.

12. The process of claim 1, wherein said cosmetic product further comprises at least one of the following technical characteristics:

hardness [shore A]: 20-60 (ASTM D2240)

tensile strength [N/mm$^2$]: 2-10 (ASTM D412)

elongation [%]: 5-15 (ASTM D412)

tear resistance [N/mm]: 10-40 (ASTM D624).

13. The process of claim 1, wherein said cosmetic product comprises at least two different carrageenans having different viscosifying capacity.

14. The process of claim 1, wherein said cosmetic product is an eyeshadow, and wherein the mixture of cosmetic powders comprises colorants, talc, mica, silica and optionally pearls.

15. The process of claim 1, wherein step ii. further comprises mixing the cosmetic powders and the emulsion in a weight ratio of 10:90 to 50:50.

16. The process of claim 15, wherein step ii. further comprises mixing the cosmetic powders and the emulsion in a weight ratio of 10:90 to 40:60.

17. The process of claim 15, wherein step ii. further comprises mixing the cosmetic powders and the emulsion in a weight ratio of about 30:70.

18. The process of claim 1, wherein said cosmetic product has all of the following technical characteristics:

hardness [shore A]: 20-60 (ASTM D2240)

tensile strength [N/mm2]: 2-10 (ASTM D412)

elongation [%]: 5-15 (ASTM D412)

tear resistance [N/mm]: 10-40 (ASTM D624).

19. The process of claim 1, wherein said cosmetic product is a solid, rubber-like, dry eyeshadow, and wherein the cosmetic powders provided in step i. are obtained by:

mixing constituents of the eyeshadow comprised of dyes, talc, mica, silica, or beads;

sieving a resulting mix to make a homogeneous particle size; and coating the mica with titanium oxide in a concentration of 20 to 70% by weight, based on a total weight of the powder mixture.

* * * * *